United States Patent [19]

Tomiyama

[11] 4,209,529

[45] Jun. 24, 1980

[54] FARNESYL CARBOXYLIC ACID α-BISABOLOL ESTER, A MUCOSAL STABILIZING COMPOSITION AND METHOD OF MANUFACTURING THE SAME

[75] Inventor: Tsuyoshi Tomiyama, Sakaki, Japan

[73] Assignee: Kotobuki Seiyaku Company Limited, Japan

[21] Appl. No.: 910,776

[22] Filed: May 30, 1978

[30] Foreign Application Priority Data

May 31, 1977 [JP] Japan .................................. 52-62765
Jun. 10, 1977 [JP] Japan .................................. 52-69063

[51] Int. Cl.$^2$ ......................... A61K 31/23; C09F 5/08
[52] U.S. Cl. .................................... 424/312; 260/410
[58] Field of Search ..................... 260/410 R; 424/312

[56] References Cited

PUBLICATIONS

Chem. Abst. 9th Coll. Index, 1972–1976, Diazene-Ethaneperoxoic acid.

*Primary Examiner*—Stanley J. Friedman
*Attorney, Agent, or Firm*—Robert E. Burns; Emmanuel J. Lobato; Bruce L. Adams

[57] ABSTRACT

A new compound, farnesyl carboxylic acid α-bisabolol ester is disclosed, which is a novel mucosal stabilizing agent showing anti-inflammative and anti-ulcerative activities. This new compound is especially useful in the treatment of gastric ulcer. The compound is synthesized by esterification of farnesyl carboxylic acid or its derivatives with α-bisabolol or a derivative thereof.

4 Claims, No Drawings

FARNESYL CARBOXYLIC ACID α-BISABOLOL ESTER, A MUCOSAL STABILIZING COMPOSITION AND METHOD OF MANUFACTURING THE SAME

BACKGROUND OF THE INVENTION

This invention relates to a novel compound, method of manufacture therefor and a new gastric mucosal stabilizing composition. More particularly, this invention concerns farnesyl carboxylic acid α-bisabolol ester, the method of manufacturing the same, its use as a gastric mucosal stabilizing agent and pharmaceutical compositions containing the new compound.

During the investigation of the active component of the essential oil of Camomilla, we became interested in the mono-cyclic tertiary sesquiterpene alcohol, α-bisabolol (I):

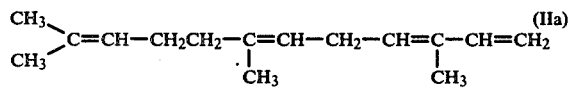

and the acyclic sesequiterpene, farnesene (IIa).

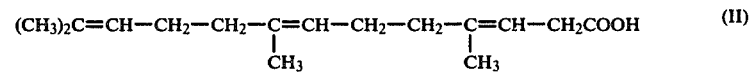

These two compounds, α-bisabolol (I) and farnesene (IIa) have been considered to be the essential components of Camomilla and these compounds have anti-inflammative and anti-ulcerative activities, and also have been reported to possess sedative or depressive activities. (Ann. Pharm. France, 33, 229 ('75)).

SUMMARY OF THE INVENTION

The principal object of the present invention is the provision of a novel gastric mucosal stabilizing agent.

Another important object of the present invention is the provision of a novel compound having advantageous pharmaceutical properties.

Still another object of the present invention is the provision of a pharmaceutical composition useful as a muscosal stabilizing agent.

Further objects of the present invention are the provisions of a pharmaceutical composition useful as an anti-inflammatory agent and a new method of treating inflammation.

Other objects of the present invention are the provisions of a pharmaceutical composition useful as an anti-peptic ulcerative agent and a new method of treating peptic ulcer.

Further important objects of the present invention are the provisions of farnesyl carboxylic acid α-bisabolol ester and a method for the manufacture thereof.

These and other objects of the invention will become apparent from the detailed description set forth below.

As a result of our studies and in accordance with the present invention we decided to try to introduce a carboxylic acid group into farnesene (IIa) and to couple the resultant farnesyl carboxylic acid with α-bisabolol (I) by esterification.

We have discovered that the resultant new esterified compound of farnesyl carboxylic acid with α-bisabolol (III) has excellent anti-inflammative and anti-ulcerative activities.

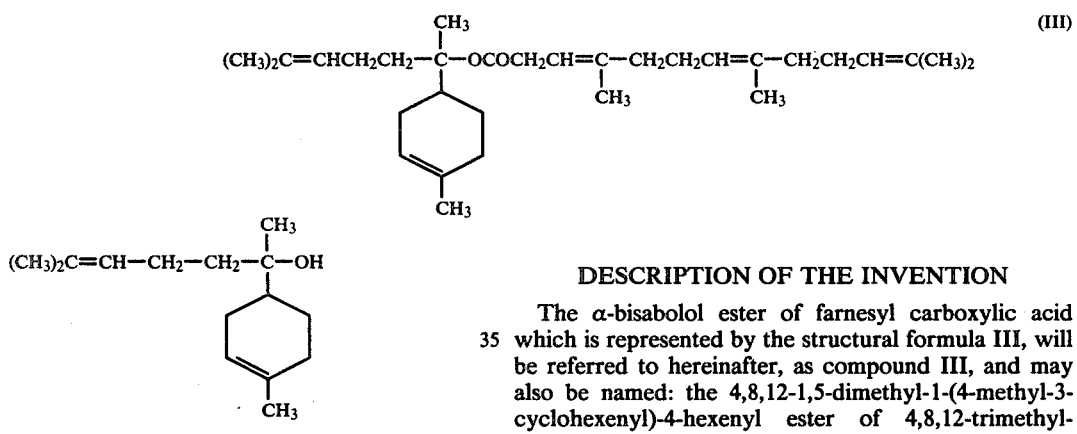

DESCRIPTION OF THE INVENTION

The α-bisabolol ester of farnesyl carboxylic acid which is represented by the structural formula III, will be referred to hereinafter, as compound III, and may also be named: the 4,8,12-1,5-dimethyl-1-(4-methyl-3-cyclohexenyl)-4-hexenyl ester of 4,8,12-trimethyl-3,7,11-tridecatrienoic acid (which can also be referred to as 3,7,11-trimethyl-2,6,10-dodecatrien-1-carboxylic acid).

Farnesyl carboxylic acid (II), which is esterified with α-bisabolol or a derivative thereof to provide the new compound III of the invention has the formula, $$(CH_3)_2C=CH-CH_2-CH_2-\underset{CH_3}{C}=CH-CH_2-CH_2-\underset{CH_3}{C}=CH-CH_2COOH \quad (II)$$

New compound III has been found to be less toxic and has a potent inhibitory effect on experimental stress and 5HT induced ulcer in animals, compared to α-bisabolol and farnesene. Also, new compound III more strongly inhibits gastric mucosal lesions induced by administration of nonsteroidal anti-inflammatory drugs, such as aspirin and indomethacin than does gefarnate. In another experiment compound III of the invention has been shown to possess mucosal stabilizing anti-inflammative, and wound-healing activities.

Pharmacological experiment 1

The gastric epithelial cell stabilizing effects of new compound III of the invention were studied in rats. Male Donryu strain rats, weighing about 200 g., were divided into five groups. Four test drugs, the compound (III) or drug of the invention, α-bisabolol (I), farnesyl carboxylic acid (II) and gefarnate as an active standard, were given orally at a dosage of 200 mg./kg., three times a day for 5 days. On the fifth day the animals were fasted for 24 hours, and submitted to pylorus ligation under light ether anethesia.

The drugs were given just after pylorus ligation orally. After 8 hours of ligation, the rats were sacrificed and gastric juice was collected. The volume of gastric juice was measured and centrifuged at 5,000 rpm. for 10 minutes under 4° C.; 2 ml. of the resulting supernatant was submitted to N-acetyl neuromatic acid (NANA) determination according to the method of D. Aminoff (D. Aminoff et. al. Biochem. J. 181: 384-392 p. 1961). The amounts of NANA in the gastric juice are shown in Table 1.

TABLE 1

| Amounts of NANA | Control | Novel Compound (III) | α-bisabolol | Farnesyl carboxylic acid | Gefarnate |
|---|---|---|---|---|---|
| free | 20.3 | 16.2* | 12.4* | 18.3 | 20.8 |
| bond | 90.1 | 71.8* | 136.3 | 80.6 | 72.8 |
| total | 110.4 | 88.9* | 148.7 | 98.6 | 93.6 |

*significantly different from the Control ($P < 0.05$)

As shown in Table 1, only the present compound (III) reduced the free, bond and total NANA levels significantly. These findings indicate that the present substance reduces the turnover rate of gastric mucosal cells and stabilizes the lysozonal membrane, with resulting proliferation of mucosa of the stomach and prevention of back diffusion, as postulated by D. V. Parke (North American Symposium on Carbenoxolone (Montreal) 16 p. (1976)).

As for gastric errosion induced by 8 hours of pyrolus ligation, only the present drug (III) of the group administered did not produce any damage to the gastric mucosa, but other drugs did.

Pharmacological experiment 2

To study the effect of the present compound on carrageenin-induced rat paw edema, the method of C. A. Winter (J. Pharmacol 141,369, (1963)) was applied. Wistar rats, weighing about 140 g. were used.

The present compound (III), α-bisabolol and farnesyl carboxylic acid were administered at a dosage of 300 mg./kg. (per os.) using a 1% CMC solution as the vehicle. The % inhibition was calculated as follows:

$$\% \text{ inhibition} = \frac{(\text{Paw-volume of control group}) - (\text{Paw-volume of test group})}{\text{paw-volume of control rat}} \times 100$$

TABLE 2

| | Maximum % Inhibition % | Increase in % of paw edema (%) |
|---|---|---|
| Compound III | 39.6 | 60.4 |
| α-Bisabolol | 11.9 | 88.1 |
| Farnesyl carboxylic acid | 23.3 | 76.7 |

As shown in Table 2, the present compound (III) showed the maximum % inhibition of carrageneen-induced rat paw edema among the test drugs. The increased rate of paw-edema of the compound (III)-treated rats (0.604) is smaller than the product of that of α-bisabolol and farnesyl carboxylic acid ($0.881 \times 0.767 = 0.675$); synergism therefore, may occur by coupling the two substances, α-bisabolol, and farnesyl carboxylic acid in the form of an ester.

Pharmacological experiment 3

To study the anti-ulcerative actions of the test drugs in experimental animals, the stress ulcer was selected. Male rats of the Wistar strain, weighing 200-250 g. were subjected to stress according to Takagi et. al. (Chem. Pharm. Bull 12,465. 1964). The four test drugs, the present compound (III), α-bisabolol (I), farnesyl carboxylic acid (II) and gefarnate were suspended in 1% methyl cellulose and were administered to the rats in a dose of 100 mg./kg. body weight per os, 30 minutes before the stress. The animals were placed in the stress box and immersed in water bath of 20°-25° C. to the level of the xiphoid process for 18 hours.

At the end of the stress the animals were removed from the stress box, killed by a blow on the head, and the stomach removed. The stomach was filled with 1% formalin solution, placed in 1% formalin solution for 15 minutes and was then cut open along the greater curvature and examined for lesions to obtain the ulcer index. The ulcer index was determined in six grades (0-5; 5 implying perforation of stomach).

The results are shown in the following table:

TABLE 3

| drugs | score |
|---|---|
| Control | 4.8 ± 0.80 |
| Compound (III) of the invention | 1.5 ± 0.50 |
| α-Bisabolol | 4.0 ± 0.25 |
| Farnesyl carboxylic acid | 2.33 ± 0.84 |
| Gefarnate | 3.83 ± 0.73 |

Pharmacological experiment 4

In the following experiments, the effects of test drugs on 5-HT induced ulcer were investigated. To induce the gastric lesion, rats were fasted for 24 hours before injection of 5-HT 30 mg./kg. S.C. The animals were sacrificed after 20 hours of 5-HT injections, and examined for lesion. The dose and route of administration of test drugs are the same as experiment 3. In the experiment, the area of lesions ($mm.^2$) were measured as the ulcer-index.

TABLE 4

| | Ulcer Index |
|---|---|
| Control | 25.75 |
| Compound (III) | 0 |

As shown in Table 4, the present compound (III), in a dose of 100 mg./kg. inhibits the occurrence of lesions completely.

Pharmacological experiment 5

The preventive activity of new compound (III) against the formation of gastric mucosal lesion induced by the gastric ulcerogenic, anti-inflammatory drugs, indomethacin and aspirin was evaluated according to Okabe et. al. (Jap. J. Pharmacol. 24 169 p. 1974, Amer. J. Dig. Dis. 20 626 1975).

The results are summarized in Table 5.

Each drug in Table 5, suspended with TWEEN 80 and 1% CMC solution, was given either intraduodenally immediately after pylorus ligation (aspirin ulcer) or orally (indomethacin ulcer) at the volume of 0.5 ml./100 g. Aspirin was given orally 10 min. after pylorus ligation. Indomethacin was given orally 10 min. after drug administration. All animals were sacrificed 7 hrs. after operation.

TABLE 5

| Ulcers | Treatment | Dose (mg./kg.) | Ulcer Index (mm.$^2$) means ± s.e. | Inhibition (%) |
|---|---|---|---|---|
|  | Control |  | 30.5 ± 3.8 |  |
|  |  | 100 | 21.4 ± 4.4 | 29.8 |
| Aspirin | Compound (III) | 300 | 16.9 ± 3.6* | 44.6 |
| (100 mg./kg. per os.) |  | 1000 | 10.6 ± 2.2* | 65.2 |
|  |  | 100 | 23.7 ± 3.2 | 22.3 |
|  | Gefarnate | 300 | 16.2 ± 2.9* | 49.9 |
|  |  | 1000 | 15.4 ± 4.4* | 49.5 |
| Indomethacin | Control |  | 46.0 ± 3.8 |  |
| (20 mg./kg., per os) | Compound (III) | 300 | 26.4 ± 5.4* | 42.6 |

*significantly different from the Control (P < 0.05))

As shown in Table 5, new compound (III) significantly inhibits gastric lesion induced by both aspirin and indomethacin. Especially in the case of aspirin, new compound (III) possesses stronger preventive activity than that of gefarnate.

Pharmacological experiment 6

The LD$_{50}$ value of the present compound in ddY strain mice was determined by the up and down method, with observations carried out for 24 hours.

The test drugs used in this experiment were suspended in 1% methyl cellulose and were given orally. The results obtained are summarized in Table 6.

TABLE 6

|  | LD$_{50}$ (per os) (mg./kg. body weight) |
|---|---|
| Compound (III) | 24.080 |
| α-Bisabolol | 3.673 |
| Farnesyl carboxylic acid | 4.262 |

The toxicity of the present new compound (III) was revealed to be about 6–7 times less than that of α-bisabolol and farnesyl carboxylic acid. The low toxicity of the present compound is especially important and advantageous.

Compound III of the present invention is chemically stable and can be administered or used orally in the form of a hard or soft capsule, tablet, powder and granule with a non-toxic pharmaceutically acceptable carrier (for example, corn starch, crystal cellulose, dextrin and cyclodextrin). Additionally, by using liquid carriers such as an edible oil, emulsifier and suspension, the compound of the invention may be given parenterally.

When the new compound of the invention is used for the treatment of peptic ulcer as a mucosal stabilizing agent, and for the treatment of inflammation as anti-inflammatory, the therapeutically effective amount comprises about 100–1,000 mg. daily for an adult. It should be understood, however, that the dosage level for a given patient depends upon the severity of the disease, route of administration, age, sex, body weight and reaction sensibility.

The compound of this invention can be obtained by esterification of the compound of formula (IV)

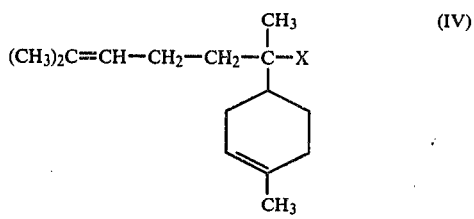

wherein X represents OH, halogens or a sulfuric acid ester group, with the compound of formula (V)

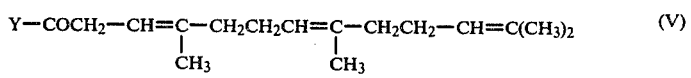

wherein Y stands for OH, OAg, an acid anhydride or lower alkoxide group.

The following processes may be carried out to obtain the novel compound of the invention.

(A) Using dehydration reagents, such as cyclohexylamide and diphenyl-phosphorylazide, the compounds wherein X is OH in formula IV and Y is OH in formula (V) are coupled or esterified in an inert solvent.

(B) In the presence of an acid scavenger, (i.e. a basic material such as pyridine) the compound IV, wherein X is OH or halogen and compound V, wherein Y is OH or OAg can be reacted.

(C) Compound IV wherein X is OX can be coupled or esterified with compound V, wherein Y is OC-COCH, by the mixed anhydride method.

(D) Trans-esterification between compound V, wherein X is OH and compound IV, wherein Y is a lower alkoxide group or sulfuric acid ester, for example, wherein X is the p-toluenesulfonate group can be also carried out.

Additionally, farnesyl carboxylic acid can be obtained by hydrolysis of the nitrile derivative after bromination of farnesol (M. Julia et. al., Bull, Soc. Chim. Fra. 1960, 1072–1079). To halogenate α-bisabolol, the method of heating carbon tetrachloride with triphenyl phosphine is recommended because dehydration and allyl rearrangement do not occur. The details of these processes are shown as follows.

EXAMPLE 1

A solution of farnesyl carboxylic acid in benzene with a small excess of thionyl chloride was heated for 1 hr. Farnesyl carboxylic acid chloride in an amount of 42.24 g., obtained after removal of benzene under reduced pressure, was dissolved in 60 ml. benzene again, and then added to a solution containing 33.08 g. of α-bisabolol in 60 ml. of benzene. To the resulting solution, anhydrous pyridine, 6.63 ml. in 30 ml. of benzene was dropped during 1 hr. in a water-ice bath, and the mixture was then refluxed for 3 hours on a water bath. After filtration of the precipitate followed by washing with 30 ml. of benzene, the resultant benzene solution was washed with water and dried over sodium sulfate.

After removal of benzene, the resulting oily residue was subjected to a spinning band column and the desired fraction obtained (180°–195° C./0.08–0.065 mmHg.). The yield was 60%. N$_D^{25}$=1.4970;

$d_{24}^{25} = 0.9337$, IR spectrum; 2930 cm.$^{-1}$ (corresponding to —CH$_3$, —CH$_2$—), 1730 cm.$^{-1}$

1650 cm.$^{-1}$ (C=C). NMR spectrum (PPM): 0.94 1.02

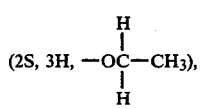

1.6–1.7

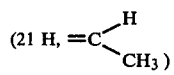

1.3–2.4 (21 H, —CH$_2$—), 4.5–5.4

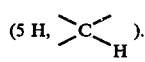

When this fraction was treated with boiling 0.5 N KOH in C$_2$H$_5$OH for 2 hrs., the substance obtained from the benzene extract was identified as α-bisabolol by gas-liquid chromatography. Additionally, the substance obtained from the benzene extracted after acidification with HCl was identical with authentic farnesyl carboxylic acid.

EXAMPLE 2

To the solution containing 1.25 g. of farnesyl carboxylic acid dissolved in 0.5 N ammonia water, 0.845 g. of silver nitrate in 3 ml. water was added. The resulting precipitate was collected by filtration and dried. The silver salt was powdered and suspended in 120 ml. of benzene, and distilled to about 60 ml. of benzene solution to remove the remaining water azeotropically. Separately, α-bisabolol chloride was prepared by adding triphenyl phosphine in an amount of 1.3 times the stoichiometric quantity, to α-bisabolol in a solution of carbon tetrachloride (1:8) and following 1 hour of reflux in water bath, the product was purified by vacuum distillation. The purified α-bisabolol chloride in an amount of 1.39 g. was dissolved in 3 ml. of benzene and added to the above solution of silver salt suspension which had been prepared previously. After 9 hours of reflux, the reaction mixture was washed with water and dried (sodium sulfate). The desired fraction was obtained by vacuum distillation (155°–156° C./0.1 mmHg) under N$_2$ gas stream.

$N_D^{25} = 1.4981$
$d_{27}^{25} = 0.9362$

EXAMPLE 3

Two and a half grams (2.50 g.) of farnesyl carboxylic acid α-bisabolol ester and 2.22 g. of α-bisabolol were dissolved in 150 ml. of xylene. A condenser and decanter (containing sodium sulfate) was attached and this reaction mixture was refluxed for 12 hours. After removal of solvent in vacuo, the residue was submitted to vacuum distillation under a N$_2$ gas stream. The fraction obtained (120°–140° C./0.03 mmHg) was identical to farnesyl carboxylic acid α-bisabolol ester obtained in previous examples.

$N_D^{25} = 1.4990$,
$d_{23}^{25} = 0.9328$.

What we desire to claim and protect by Letters Patent is:

1. Farnesyl carboxylic acid α-bisabolol ester of the formula,

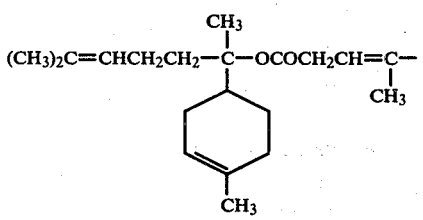
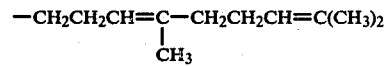

2. A gastric mucosal stabilizing composition comprising an amount effective to stabilize gastric mucosa of farnesyl carboxylic acid α-bisabolol ester in combination with a pharmaceutically acceptable carrier.

3. A method for treating peptic ulcer comprising administering to a mammal an amount of farnesyl carboxylic acid α-bisabolol ester as defined in claim 1 effective as an anti-peptic ulcerative agent.

4. A method for treating inflammations comprising administering to a mammal farnesyl carboxylic acid α-bisabolol ester as defined in claim 1 in an amount effective to reduce said inflammation.

* * * * *